(12) United States Patent
Mizunashi et al.

(10) Patent No.: US 7,557,202 B2
(45) Date of Patent: Jul. 7, 2009

(54) DNA FRAGMENTS CONTAINING GENE HAVING FUNCTION RELATING TO AUTONOMOUS PROLIFERATION OF PLASMID

(75) Inventors: Wataru Mizunashi, Kanagawa (JP); Fujio Yu, Kanagawa (JP)

(73) Assignee: Mitsubishi Rayon Co., Ltd., Tokyo (JP)

( * ) Notice: Subject to any disclaimer, the term of this patent is extended or adjusted under 35 U.S.C. 154(b) by 628 days.

(21) Appl. No.: 10/482,156

(22) PCT Filed: Jul. 3, 2002

(86) PCT No.: PCT/JP02/06732

§ 371 (c)(1),
(2), (4) Date: Jan. 5, 2004

(87) PCT Pub. No.: WO03/004639

PCT Pub. Date: Jan. 16, 2003

(65) Prior Publication Data

US 2004/0248119 A1    Dec. 9, 2004

(30) Foreign Application Priority Data

Jul. 5, 2001    (JP) ............................. 2001-204628

(51) Int. Cl.
*C07H 21/04* (2006.01)
*C12N 1/20* (2006.01)
*C12N 15/00* (2006.01)

(52) U.S. Cl. ................. 536/23.7; 435/252.3; 435/320.1

(58) Field of Classification Search ................. 536/23.7
See application file for complete search history.

(56) References Cited

U.S. PATENT DOCUMENTS

| 4,920,054 A | 4/1990 | Kozlowski et al. |
| 4,952,500 A | 8/1990 | Finnerty et al. |
| 5,565,333 A * | 10/1996 | Devauchelle et al. ........ 435/69.1 |
| 5,654,180 A * | 8/1997 | Beppu et al. ................ 435/129 |

FOREIGN PATENT DOCUMENTS

| EP | 0 502 476 A2 | 9/1992 |
| JP | 4-148685 | 5/1992 |
| JP | 5-64589 | 3/1993 |
| JP | 5-68566 | 3/1993 |
| WO | 02/055709 | 7/2002 |

OTHER PUBLICATIONS

Hirasawa et al, Improvement of Desulfurization Activity in Rhodococcus erythropolis KA2-5-1 by Genetic Engineering, Feb. 2001, Biosci. Biotechnol. Biochem, 65, 239-246.*
Renault et al. Gene 183 (1996) 175-182.*
Boros et al Gene 30 (1984) 257-260.*
Xia et al. Mol MIcrobiol. (Mar. 1991);5(3):-631-640.*
Leonhardt et al. Gene 94 (1990) 1:121-124.*
Stolt et al. Nucleic acids research (1997) 25: 3840-6.*
Hirasawa et al. GenEmbl Database Accession #ABO40101 Apr. 6, 2001—See attached sequence search.*
Inuzuka et al. EMBO Journal. (1985) vol. 4 pp. 2301-2307.*
Amersham Pharmacia Biotech Catalog 1998 p. 374, 378-379.*
Swiss-Prot accession #P03067. Jul. 21, 1986.*
Frey et al. Gene. (1992) vol. 113 pp. 101-106.*
Frey et al. Gene. (1992) vol. 113 pp.101-106.*
Kazuaki Hirasawa, et al., "Improvement of Desulfurization Activity in Rhodococcus erythropolis KA2-5-1 by Genetic Engineering", Biosci. Biotechnol. Biochem., vol. 65, No. 2, pp. 239-246.
M.E. Vogt Singer, et al., "Construction of an *Escherichia coli*-rhodococcus shuttle vector and plasmid transformation in rhodococcus spp.", Journal of Bacteriology, vol. 170, No. 2, pp. 638-645.
Richard Meyer, et al., "Properties of R1162, a broad-host-range, high-copy-number plasmid", Journal of Bacteriology, vol. 150, No. 2, pp. 552-562 1982.

* cited by examiner

*Primary Examiner*—Mark Navarro
(74) *Attorney, Agent, or Firm*—Oblon, Spivak, McClelland, Maier & Neustadt, P.C.

(57) ABSTRACT

Provided are a DNA fragment containing a gene relating the autonomous replication of a plasmid, and a DNA fragment containing a gene relating to the autonomous replication of a plasmid wherein a mutation point capable of increasing the number of copies of a plasmid is present in at least one site in the gene. Also provided are a DNA fragment containing a gene having a function relating to the autonomous replication of a plasmid within the bacteria of the genus *Rhodococcus*, a DNA fragment wherein a mutation point capable of increasing the number of copies of a plasmid is present in at least one site in the gene, and a plasmid carrying a DNA fragment wherein a mutation point capable of increasing the number of copies of a plasmid is present in at least one site of the gene.

13 Claims, 1 Drawing Sheet

SEQUENCE LISTING

<160> NUMBER OF SEQ ID NOS: 10

<210> SEQ ID NO 1
<211> LENGTH: 2582
<212> TYPE: DNA
<213> ORGANISM: Rhodococcus rhodochrous

<400> SEQUENCE: 1
cgatggcaag ccaccgcgaa gcggtggcgc ggcagaacct cgttttgccc ctgaggaggt        60

-continued

```
gacgcgaatg catgaagcat gtcgcacttg cgcgccttgt cctgttatct gtaagatcga    120
cccctggtgt acctcgtgca cccaaaatca ggcccggtgg ttcctttgga cccgggcctt    180
cgttatttcc acgccagccc gagctccgcc cgctcgtgca agcgtcatgc tcttcgtccg    240
tgatcaagac ctccgaacct atggccggcc aaccccctcg ggttgcgtcg gcctgacccg    300
ttctagggcg tctacgcggc cgcttttccca ctccgtccat accaaccccc gcaccaaagg    360
tccgggggtt ttttcatgcc cggattcggt cgcggctgcg cctcgacggt ctccggttgc    420
ccaaggaggc acccatgact tgctccacct gctcctcgcc tgccccgaa ccgcgaccgt    480
cgcgcaaaga ggcggtccag caactcgcga tccgatcgct ggcgttcttg tttcgccact    540
gcacacgaat cgccctgaac gaagtggtcc aagaactgat ccgcatcaag ttcggcggtt    600
gaccgcggac gtgcacctgt agagcgggtt gcagcgagac accgatgaac cactctccgc    660
tgcctaggcg acccggttct ggaaagatca tcaccgagtg tccggcccca cccctgcgg    720
gccggacact catctgtatg gcagcgtgcc tcccttcctg cccttcccac tgatcgtttc    780
ctcctgccaa aaatcgggac acacctcttg cagaagttct gacacccggg aaaggccggc    840
cgaaaggggg cgctcaccga ccactctgat cgagaagttc tgccgcaccc accagccgta    900
cccgccaaac cttccgcagt cccagccgta cgaaacggtc tcgtgccact ccaccggccc    960
tggtgtcgat cgactacaaa ccaagatccc cacacacctc atgcactaaa gctgcgacca   1020
cgaagaacaa ggtggtccgg gtaagacgga agggagtttt cccaggaggg tcgccgaaac   1080
atctgacttg gttggcgtgt cctacataaa aaaattgatc ttgcgtgtga gggtgtcacg   1140
catggatatg agcgggggat ctctcagtgg ggactgggag cagttgtggc tgcctctgtg   1200
gccgctcgca acgacgatt tgttgcttgg ggtctaccgg atgcctcgcc aggatgcgct   1260
cgatcggcgc taccttgagg ccaatccgca ggcgctgagc aatctcctcg tcgtcgatgt   1320
cgatcatcca gacgcggcac tgcgggctct gtctgccgcc ggcaaccatc ccttgccgaa   1380
cgcgatcgtg gaaaacccgc gcaatggaca cgcacatgcg gtgtgggcat tgaccgaacc   1440
tttcacgcgc accgagtacg ccagacgtaa gccactcgct tatgccgcag cggtaaacga   1500
ggggctgcgt cgagctgtcg atggcgatgc cgcctattcg gggttgatga cgaagaaccc   1560
gactcactca gcctgggaca cacactggat ccacgccgag actcgatcgc tggcagatct   1620
cgaacatgac ctcggaaagc atatgccgcc accccggtgg cgacagagca acgtcgtcg   1680
cgaagaccca gtcggactcg gacgtaattg catgctcttc gagacggcac gcacttgggc   1740
ataccgcgaa ttgcgttgcc attggggaga tcccgaaggt ttagggaaag caattcaggt   1800
cgaagccgca gaccttaacg ctgccttctc tgagcctttg ccggtaagcg aagtacgagc   1860
tatcgcagcc agcattcacc gctggatcgt caccaagtcc cgcatgtggg ccgatggccc   1920
tgcggtttac gaagccacct tcgtcgctat ccaatccgct cgcggacgca agatgacgga   1980
gaagaagcgc gaggccaatc gtcgccgtgc aacgaagtac gaccgcgacc tcgtgaggaa   2040
ggaggcgacc gatgggagct gagacgccgg cccggcgaac ccgcacagct cgcgaagtgg   2100
cggaacgaat cggtgcgtcc ccacgcacgg tgcggcgcat catcgcggag cctcgagctt   2160
catacgaagc tcgagcagct gaacgtcgaa agcaagtact cgaactccgt gcagcgggga   2220
tgaagctgcg tgagatcgcg gcggaggtag gtatgtcggt cggtggagta gggacgatcc   2280
tgcatcacgc ccgtaagacc gagcagtcta aggctgaagg agctatggca tgaacgacgc   2340
catatcggcc cgcatcactg caatgcaggc ccaactgacg gctgtacata ccgagctacg   2400
```

```
tgctctagcg gagctggtgg acatgcttga tgccgacgct ctcgatgctg agaccgaaga    2460
ttcagtgcgc gaagtgatcg actccctggc agacgctggg cgagctctag ctggcgccga    2520
cgagccgctc caggccgcaa ttcatcacgc ccggcgactg ccttagtcag cttctgtccg    2580
at                                                                   2582

<210> SEQ ID NO 2
<211> LENGTH: 2582
<212> TYPE: DNA
<213> ORGANISM: Rhodococcus rhodochrous

<400> SEQUENCE: 2
cgatggcaag ccaccgcgaa gcggtggcgc ggcagaacct cgttttgccc ctgaggaggt      60
gacgcgaatg catgaagcat gtcgcacttg cgcgccttgt cctgttatct gtaagatcga     120
cccctggtgt acctcgtgca cccaaaatca ggcccggtgg ttcctttgga cccgggcctt     180
cgttatttcc acgccagccc gagctccgcc cgctcgtgca agcgtcatgc tcttcgtccg     240
tgatcaagac ctccgaacct atggccggcc aaccccctcg ggttgcgtcg gcctgacccg     300
ttctagggcg tctacgcggc cgcttttccca ctccgtccat accaaccccc gcaccaaagg    360
tccgggggtt ttttcatgcc cggattcggt cgcggctgcg cctcgacggt ctccggttgc     420
ccaaggagga acccatgact tgctccacct gctcctcgcc tgcccccgaa ccgcgaccgt     480
cgcgcaaaga ggcggtccag caactcgcga tccgatcgct ggcgttcttg tttcgccact     540
gcacacgaat cgccctgaac gaagtggtcc aagaactgat ccgcatcaag ttcggcggtt     600
gaccgcggac gtgcacctgt agagcgggtt gcagcgagac accgatgaac cactctccgc     660
tgcctaggcg accggttcct ggaaagatca tcaccgagtg tccggcccca cccctgcgg      720 gccggacact catctgtatg gcagcgtgcc tcccttcctg cccttcccac tgatcgtttc     780
ctcctgccaa aaatcgggac acacctcttg cagaagttct gacacccggg aaaggccggc    840
cgaaaggggg cgctcaccga ccactctgat cgagaagttc tgccgcaccc accagccgta     900
cccgccaaac cttccgcagt cccagccgta cgaaacggtc tcgtgccact ccaccggccc     960
tggtgtcgat cgactacaaa ccaagatccc cacacacctc atgcactaaa gctgcgacca    1020
cgaagaacaa ggtggtccgg gtaagacgga agggagtttt cccaggaggg tcgccgaaac   1080
atctgacttg gttggcgtgt cctacataaa aaaattgatc ttgcgtgtga gggtgtcacg   1140
catggatatg agcgggggat ctctcagtgg ggactgggag cagttgtggc tgcctctgtg   1200
gccgctcgca acggacgatt tgttgcttgg ggtctaccgg atgcctcgcc aggatgcgct   1260
cgatcggcgc taccttgagg ccaatccgca ggcgctgagc aatctcctcg tcgtcgatgt   1320
cgatcatcca gacgcggcac tgcgggctct gtctgccgcc ggcaaccatc ccttgccgaa   1380
cgcgatcgtg gaaacccgc gcaatggaca cgcacatgcg gtgtgggcat tgaccgaacc   1440
tttcacgcgc accgagtacg ccagacgtaa gccactcgct tatgccgcag cggtaaacga   1500
ggggctgcgt cgagctgtcg atggcgatgc cgcctattcg gggttgatga cgaagaaccc   1560
gactcactca gcctgggaca cacactggat ccacgccgag actcgatcgc tggcagatct   1620
cgaacatgac ctcggaaagc atatgccgcc accccggtgg cgacagagca acgtcgtcg    1680 cgaagaccca gtcggactcg gacgtaattg catgctcttc gagacggcac gcacttgggc   1740
ataccgcgaa ttgcgttgcc attggggaga tcccgaaggt ttagggaaag caattcaggt   1800
cgaagccgca gaccttaacg ctgccttctc tgagcctttg ccggtaagcg aagtacgagc   1860
tatcgcagcc agcattcacc gctggatcgt caccaagtcc cgcatgtggg ccgatggccc   1920
```

| | |
|---|---:|
| tgcggtttac gaagccacct tcgtcgctat ccaatccgct cgcggacgca agatgacgga | 1980 |
| gaagaagcgc gaggccaatc gtcgccgtgc aacgaagtac gaccgcgacc tcgtgaggaa | 2040 |
| ggaggcgacc gatgggagct gagacgccgg cccggcgaac ccgcacagct cgcgaagtgg | 2100 |
| cggaacgaat cggtgcgtcc ccacgcacgg tgcggcgcat catcgcggag cctcgagctt | 2160 |
| catacgaagc tcgagcagct gaacgtcgaa agcaagtact cgaactccgt gcgagcggga | 2220 |
| tgaagctgcg tgagatcgcg gcggaggtag gtatgtcggt ctgtggagta gggacgatcc | 2280 |
| tgcatcacgc ccgtaagacc gagcagtcta aggctgaagg agctatggca tgaacgacgc | 2340 |
| catatcggcc cgcatcactg caatgcaggc ccaactgacg gctgtacata ccgagctacg | 2400 |
| tgctctagcg gagctggtgg acatgcttga tgccgacgct ctcgatgctg agaccgaaga | 2460 |
| ttcagtgcgc gaagtgatcg actccctggc agacgctggg cgagctctag ctggcgccga | 2520 |
| cgagccgctc caggccgcaa ttcatcacgc ccggcgactg ccttagtcag cttctgtccg | 2580 |
| at | 2582 |

<210> SEQ ID NO 3
<211> LENGTH: 1581
<212> TYPE: DNA
<213> ORGANISM: Rhodococcus rhodochrous

<400> SEQUENCE: 3

| | |
|---|---:|
| cgtacgaaac ggtctcgtgc cactccaccg gccctggtgt cgatcgacta caaaccaaga | 60 |
| tccccacaca cctcatgcac taaagctgcg accacgaaga acaaggtggt ccgggtaaga | 120 |
| cggaagggag ttttcccagg agggtcgccg aaacatctga cttggttggc gtgtcctaca | 180 |
| taaaaaatt gatcttgcgt gtgagggtgt cacgcatgga tatgagcggg ggatctctca | 240 |
| gtggggactg ggagcagttg tggctgcctc tgtggccgct cgcaacggac gatttgttgc | 300 |
| ttggggtcta ccgatgcct cgccaggatg cgctcgatcg gcgctacctt gaggccaatc | 360 |
| cgcaggcgct gagcaatctc ctcgtcgtcg atgtcgatca tccagacgcg gcactgcggg | 420 |
| ctctgtctgc cgccggcaac catcccttgc gaacgcgat cgtggaaaac ccgcgcaatg | 480 |
| gacacgcaca tgcggtgtgg gcattgaccg aacctttcac gcgcaccgag tacgccagac | 540 |
| gtaagccact cgcttatgcc gcagcggtaa acgaggggcg gcgtcgagct gtcgatggcg | 600 |
| atgccgccta ttcggggttg atgacgaaga acccgactca ctcagcctgg gacacacact | 660 |
| ggatccacgc cgagactcga tcgctggcag atctcgaaca tgacctcgga aagcatatgc | 720 |
| cgccaccccg gtggcgacag agcaaacgtc gtcgcgaaga cccagtcgga ctcggacgta | 780 |
| attgcatgct cttcgagacg gcacgcactt gggcataccg cgaattgcgt tgccattggg | 840 |
| gagatcccga aggtttaggg aaagcaattc aggtcgaagc cgcagacctt aacgctgcct | 900 |
| tctctgagcc tttgccggta agcgaagtac gagctatcgc agccagcatt caccgctgga | 960 |
| tcgtcaccaa gtcccgcatg tgggccgatg ccctgcggt ttacgaagcc accttcgtcg | 1020 |
| ctatccaatc cgctcgcgga cgcaagatga cggagaagaa gcgcgaggcc aatcgtcgcc | 1080 |
| gtgcaacgaa gtacgaccgc gacctcgtga ggaaggaggc gaccgatggg agctgagacg | 1140 |
| ccggcccggc gaaccgcac agctcgcgaa gtggcggaac gaatcggtgc gtccccacgc | 1200 |
| acggtgcggc gcatcatcgc ggagcctcga gcttcatacg aagctcgagc agctgaacgt | 1260 |
| cgaaagcaag tactcgaact ccgtgcgagc gggatgaagc tgcgtgagat cgcggcggag | 1320 |
| gtaggtatgt cggtcggtgg agtagggacg atcctgcatc acgcccgtaa gaccgagcag | 1380 |

```
tctaaggctg aaggagctat ggcatgaacg acgccatatc ggcccgcatc actgcaatgc    1440
aggcccaact gacggctgta cataccgagc tacgtgctct agcggagctg gtggacatgc    1500
ttgatgccga cgctctcgat gctgagaccg aagattcagt gcgcgaagtg atcgactccc    1560
tggcagacgc tgggcgagct c                                              1581

<210> SEQ ID NO 4
<211> LENGTH: 1581
<212> TYPE: DNA
<213> ORGANISM: Rhodococcus rhodochrous

<400> SEQUENCE: 4
cgtacgaaac ggtctcgtgc cactccaccg gccctggtgt cgatcgacta caaaccaaga      60
tccccacaca cctcatgcac taaagctgcg accacgaaga acaaggtggt ccgggtaaga    120
cggaagggag ttttcccagg agggtcgccg aaacatctga cttggttggc gtgtcctaca    180 taaaaaatt gatcttgcgt gtgagggtgt cacgcatgga tatgagcggg ggatctctca     240
gtggggactg ggagcagttg tggctgcctc tgtggccgct cgcaacggac gatttgttgc    300
ttggggtcta ccggatgcct cgccaggatg cgctcgatcg gcgctacctt gaggccaatc    360
cgcaggcgct gagcaatctc ctcgtcgtcg atgtcgatca tccagacgcg gcactgcggg    420
ctctgtctgc cgccggcaac catcccttgc gaacgcgat cgtggaaaac ccgcgcaatg     480
gacacgcaca tgcggtgtgg gcattgaccg aacctttcac gcgcaccgag tacgccagac    540
gtaagccact cgcttatgcc gcagcggtaa acgagggct cgtcgagct gtcgatggcg      600 atgccgccta ttcggggttg atgacgaaga acccgactca ctcagcctgg acacacact    660 ggatccacgc cgagactcga tcgctggcag atctcgaaca tgacctcgga agcatatgc     720 cgccaccccg gtgcgacag agcaaacgtc gtcgcgaaga cccagtcgga ctcggacgta     780
attgcatgct cttcgagacg gcacgcactt gggcataccg cgaattgcgt tgccattggg    840
gagatcccga aggtttaggg aaagcaattc aggtcgaagc cgcagacctt aacgctgcct    900
tctctgagcc tttgccggta agcgaagtac gagctatcgc agccagcatt caccgctgga    960
tcgtcaccaa gtcccgcatg tgggccgatg gccctgcggt ttacgaagcc accttcgtcg   1020
ctatccaatc cgctcgcgga cgcaagatga cggagaagaa gcgcgaggcc aatcgtcgcc   1080
gtgcaacgaa gtacgaccgc gacctcgtga ggaaggaggc gaccgatggg agctgagacg   1140
ccggcccggc gaaccccgcac agctcgcgaa gtggcggaac gaatcggtgc gtccccacgc   1200
acggtgcggc gcatcatcgc ggagcctcga gcttcatacg aagctcgagc agctgaacgt   1260
cgaaagcaag tactcgaact ccgtgcgagc gggatgaagc tgcgtgagat cgcggcggag   1320
gtaggtatgt cggtctgtgg agtagggacg atcctgcatc acgcccgtaa gaccgagcag   1380
tctaaggctg aaggagctat ggcatgaacg acgccatatc ggcccgcatc actgcaatgc   1440
aggcccaact gacggctgta cataccgagc tacgtgctct agcggagctg gtggacatgc   1500
ttgatgccga cgctctcgat gctgagaccg aagattcagt gcgcgaagtg atcgactccc   1560
tggcagacgc tgggcgagct c                                             1581

<210> SEQ ID NO 5
<211> LENGTH: 921
<212> TYPE: DNA
<213> ORGANISM: Rhodococcus rhodochrous

<400> SEQUENCE: 5
atggatatga gcggggatc tctcagtggg gactgggagc agttgtggct gcctctgtgg      60
```

```
ccgctcgcaa cggacgattt gttgcttggg gtctaccgga tgcctcgcca ggatgcgctc    120
gatcggcgct accttgaggc caatccgcag gcgctgagca atctcctcgt cgtcgatgtc    180
gatcatccag acgcggcact gcgggctctg tctgccgccg gcaaccatcc cttgccgaac    240
gcgatcgtgg aaaacccgcg caatggacac gcacatgcgg tgtgggcatt gaccgaacct    300
ttcacgcgca ccgagtacgc cagacgtaag ccactcgctt atgccgcagc ggtaaacgag    360
gggctgcgtc gagctgtcga tggcgatgcc gcctattcgg ggttgatgac gaagaacccg    420
actcactcag cctgggacac acactggatc cacgccgaga ctcgatcgct ggcagatctc    480
gaacatgacc tcggaaagca tatgccgcca ccccggtggc gacagagcaa acgtcgtcgc    540
gaagacccag tcggactcgg acgtaattgc atgctcttcg agacggcacg cacttgggca    600
taccgcgaat tgcgttgcca ttggggagat cccgaaggtt tagggaaagc aattcaggtc    660
gaagccgcag accttaacgc tgccttctct gagcctttgc cggtaagcga agtacgagct    720
atcgcagcca gcattcaccg ctggatcgtc accaagtccc gcatgtgggc cgatggccct    780
gcggtttacg aagccacctt cgtcgctatc caatccgctc gcggacgcaa gatgacggag    840
aagaagcgcg aggccaatcg tcgccgtgca acgaagtacg accgcgacct cgtgaggaag    900
gaggcgaccg atgggagctg a                                              921
```

<210> SEQ ID NO 6
<211> LENGTH: 306
<212> TYPE: PRT
<213> ORGANISM: Rhodococcus rhodochrous

<400> SEQUENCE: 6

```
Met Asp Met Ser Gly Gly Ser Leu Ser Gly Asp Trp Glu Gln Leu Trp
1               5                   10                  15
Leu Pro Leu Trp Pro Leu Ala Thr Asp Asp Leu Leu Leu Gly Val Tyr
            20                  25                  30
Arg Met Pro Arg Gln Asp Ala Leu Asp Arg Arg Tyr Leu Glu Ala Asn
        35                  40                  45
Pro Gln Ala Leu Ser Asn Leu Leu Val Val Asp Val Asp His Pro Asp
    50                  55                  60
Ala Ala Leu Arg Ala Leu Ser Ala Ala Gly Asn His Pro Leu Pro Asn
65                  70                  75                  80
Ala Ile Val Glu Asn Pro Arg Asn Gly His Ala His Ala Val Trp Ala
                85                  90                  95
Leu Thr Glu Pro Phe Thr Arg Thr Glu Tyr Ala Arg Arg Lys Pro Leu
            100                 105                 110
Ala Tyr Ala Ala Val Asn Glu Gly Leu Arg Arg Ala Val Asp Gly
        115                 120                 125
Asp Ala Ala Tyr Ser Gly Leu Met Thr Lys Asn Pro Thr His Ser Ala
    130                 135                 140
Trp Asp Thr His Trp Ile His Ala Glu Thr Arg Ser Leu Ala Asp Leu
145                 150                 155                 160
Glu His Asp Leu Gly Lys His Met Pro Pro Arg Trp Arg Gln Ser
                165                 170                 175
Lys Arg Arg Arg Glu Asp Pro Val Gly Leu Gly Arg Asn Cys Met Leu
            180                 185                 190
Phe Glu Thr Ala Arg Thr Trp Ala Tyr Arg Glu Leu Arg Cys His Trp
        195                 200                 205
Gly Asp Pro Glu Gly Leu Gly Lys Ala Ile Gln Val Glu Ala Ala Asp
```

```
                210                 215                 220
Leu Asn Ala Ala Phe Ser Glu Pro Leu Pro Val Ser Glu Val Arg Ala
225                 230                 235                 240

Ile Ala Ala Ser Ile His Arg Trp Ile Val Thr Lys Ser Arg Met Trp
                245                 250                 255

Ala Asp Gly Pro Ala Val Tyr Glu Ala Thr Phe Val Ala Ile Gln Ser
            260                 265                 270

Ala Arg Gly Arg Lys Met Thr Glu Lys Lys Arg Glu Ala Asn Arg Arg
        275                 280                 285

Arg Ala Thr Lys Tyr Asp Arg Asp Leu Val Arg Lys Glu Ala Thr Asp
290                 295                 300

Gly Ser
305

<210> SEQ ID NO 7
<211> LENGTH: 282
<212> TYPE: DNA
<213> ORGANISM: Rhodococcus rhodochrous

<400> SEQUENCE: 7
atgggagctg agacgccggc ccggcgaacc cgcacagctc gcgaagtggc ggaacgaatc      60
ggtgcgtccc cacgcacggt gcggcgcatc atcgcggagc ctcgagcttc atacgaagct     120
cgagcagctg aacgtcgaaa gcaagtactc gaactccgtg cgagcgggat gaagctgcgt     180
gagatcgcgg cggaggtagg tatgtcggtc ggtggagtag gacgatcct gcatcacgcc      240 cgtaagaccg agcagtctaa ggctgaagga gctatggcat ga                        282

<210> SEQ ID NO 8
<211> LENGTH: 93
<212> TYPE: PRT
<213> ORGANISM: Rhodococcus rhodochrous

<400> SEQUENCE: 8

Met Gly Ala Glu Thr Pro Ala Arg Arg Thr Arg Thr Ala Arg Glu Val
1               5                   10                  15

Ala Glu Arg Ile Gly Ala Ser Pro Arg Thr Val Arg Arg Ile Ile Ala
            20                  25                  30

Glu Pro Arg Ala Ser Tyr Glu Ala Arg Ala Ala Glu Arg Lys Gln
        35                  40                  45

Val Leu Glu Leu Arg Ala Ser Gly Met Lys Leu Arg Glu Ile Ala Ala
50                  55                  60

Glu Val Gly Met Ser Val Gly Gly Val Gly Thr Ile Leu His His Ala
65                  70                  75                  80

Arg Lys Thr Glu Gln Ser Lys Ala Glu Gly Ala Met Ala
            85                  90

<210> SEQ ID NO 9
<211> LENGTH: 282
<212> TYPE: DNA
<213> ORGANISM: Rhodococcus rhodochrous

<400> SEQUENCE: 9
atgggagctg agacgccggc ccggcgaacc cgcacagctc gcgaagtggc ggaacgaatc      60
ggtgcgtccc cacgcacggt gcggcgcatc atcgcggagc ctcgagcttc atacgaagct     120
cgagcagctg aacgtcgaaa gcaagtactc gaactccgtg cgagcgggat gaagctgcgt     180
gagatcgcgg cggaggtagg tatgtcggtc tgtggagtag gacgatcct gcatcacgcc      240
```

-continued

```
cgtaagaccg agcagtctaa ggctgaagga gctatggcat ga                    282

<210> SEQ ID NO 10
<211> LENGTH: 93
<212> TYPE: PRT
<213> ORGANISM: Rhodococcus rhodochrous

<400> SEQUENCE: 10

Met Gly Ala Glu Thr Pro Ala Arg Arg Thr Arg Thr Ala Arg Glu Val
1               5                   10                  15

Ala Glu Arg Ile Gly Ala Ser Pro Arg Thr Val Arg Arg Ile Ile Ala
            20                  25                  30

Glu Pro Arg Ala Ser Tyr Glu Ala Arg Ala Ala Glu Arg Arg Lys Gln
        35                  40                  45

Val Leu Glu Leu Arg Ala Ser Gly Met Lys Leu Arg Glu Ile Ala Ala
    50                  55                  60

Glu Val Gly Met Ser Val Ser Gly Val Gly Thr Ile Leu His His Ala
65                  70                  75                  80

Arg Lys Thr Glu Gln Ser Lys Ala Glu Gly Ala Met Ala
                85                  90
```

US 7,557,202 B2

DNA FRAGMENTS CONTAINING GENE HAVING FUNCTION RELATING TO AUTONOMOUS PROLIFERATION OF PLASMID

FIELD OF THE INVENTION

The present invention relates to a DNA fragment containing a gene having a function relating to the autonomous replication of a plasmid. The present invention further relates to a DNA fragment, which contains a gene having a function relating to the autonomous replication of a plasmid within the bacteria of the genus *Rhodococcus* and wherein a mutation point capable of increasing the number of copies of a plasmid is present in at least one site in the gene. The present invention also relates to a multiple-copy-number plasmid vector carrying the DNA fragment.

BACKGROUND ART

Microorganisms belonging to the genus *Rhodococcus* are known as microbial catalysts to hydrate nitriles so as to produce corresponding amides or acids. Moreover, the microorganisms also exert a great variety of properties in producing enzymes involved in degradation of PCB (polychlorinated biphenyl) or the like or desulfurization of crude oil, as well as producing biosurfactants which are used, for example, for effluent treatment, so that they are known to be industrially very useful microorganisms.

In addition, microorganisms belonging to the species of *Rhodococcus rhodochrous* are known to have extremely highly efficient nitrile hydration activity, so that they are industrially utilized as catalysts for producing acrylamide through biotechnology.

The term "ATCC" where it appears in the specification below refers to the American Type Culture Collection® or ATCC®.

Under such circumstances, the development of host vector systems of the genus *Rhodococcus* has been expected, and some such systems have been developed. Examples of industrially useful plasmid vectors of bacteria of the genus *Rhodococcus* include plasmid pRC001 carried by *Rhodococcus rhodochrous* ATCC4276, pRC002 carried by *Rhodococcus rhodochrous* ATCC14349, pRC003 carried by *Rhodococcus rhodochrous* ATCC14348, plasmid pRC004 (see Japanese Patent No. 2983602) carried by *Rhodococcus rhodochrous* IFO3338, and composite plasmid vectors pK1, pK2, pK3 and pK4 (see JP Patent Publication (Kokai) No. 5-64589 A (1993)) comprising a plasmid DNA region capable of duplicating and replicating within the cells of *Escherichia coli* and a DNA region containing a drug resistance gene and pRC020 (see JP Patent Publication (Kokai) No. 9-28379 A (1997)) carried by *Rhodococcus erythropolis* IFO12320. When a useful gene is introduced into a plasmid vector and then expressed by bacteria of the genus *Rhodococcus* as a host, it is known that the expression level of this useful gene is almost proportional to the number of copies of the plasmid vector. However, the number of copies of these plasmids within the cells of the bacteria of the genus *Rhodococcus* is around 2 to 6, which is not always sufficient to cause high expression of a foreign gene.

SUMMARY OF THE INVENTION

Introducing a multiple-copy-number plasmid vector having a useful gene inserted therein into cells is expected to result in a high gene amplification effect.

An object of the present invention is to provide a DNA fragment which is derived from a plasmid capable of autonomously replicating within the bacteria of the genus *Rhodococcus* and containing a gene relating to the autonomous replication of a plasmid. Specifically, it is an object of the present invention to provide a DNA fragment derived from a plasmid capable of autonomously replicating within the bacteria of the genus *Rhodococcus* and containing a gene involved in the autonomous replication of a plasmid, wherein a mutation point capable of increasing the number of copies of a plasmid is present in at least one site in the gene.

We have completed the present invention by revealing a DNA region containing a gene having a function relating to the autonomous replication of a plasmid within the bacteria of the genus *Rhodococcus*, and obtaining a DNA fragment wherein a mutation point capable of increasing the number of copies of a plasmid is present in at least one site in the gene. That is, the present invention relates to a DNA fragment derived from a plasmid selected from plasmids pRC001, pRC002, pRC003 and pRC004, and containing a gene having a function relating to the autonomous replication of a plasmid within the bacteria of the genus *Rhodococcus*. The present invention further relates to a DNA fragment derived from a plasmid capable of autonomously replicating within the bacteria of the genus *Rhodococcus* and containing a gene relating to the autonomous replication of a plasmid, wherein a mutation point capable of increasing the number of copies of a plasmid is present in at least one site in the gene. The present invention is as follows.

(1) A DNA fragment, which is derived from a plasmid selected from plasmids pRC001, pRC002, pRC003 and pRC004, and contains a gene having a function relating to the autonomous replication of a plasmid within the bacteria of the genus *Rhodococcus*.

(2) The DNA fragment of (1), which has a size of 1.6 kb, and has cleavage points for restriction enzymes Spl I and Sac I at its ends.

(3) The DNA fragment of (1), which has a size of 1.7 kb, and has cleavage points for restriction enzymes Sma I and Sac I at its ends.

(4) The DNA fragment of (1), which has a size of 1.9 kb, and has cleavage points for a restriction enzyme Sma I at both of its ends.

(5) The DNA fragment of (1), which has a size of 2.3 kb, and has cleavage points for a restriction enzyme Sac I at both of its ends.

(6) The DNA fragment of (1), which is contained in pRC004, contains a gene having a function relating to the autonomous replication of a plasmid within the bacteria of the genus *Rhodococcus* and consists of the nucleotide sequence of SEQ ID NO: 1.

(7) The DNA fragment of (1), which is contained in pRC004, contains a gene having a function relating to the autonomous replication of a plasmid within the bacteria of the genus *Rhodococcus* and consists of the nucleotide sequence of SEQ ID NO: 3.

(8) The DNA fragment of (1), which is contained in pRC004, contains a gene having a function relating to the autonomous replication of a plasmid within the bacteria of the genus *Rhodococcus*, and consists of the nucleotide sequence of SEQ ID NO: 7.

(9) The DNA fragment of any one of (1) to (8), wherein a mutation point capable of increasing the number of copies of a plasmid is present in at least one site.

(10) The DNA fragment of (9), wherein a mutation point capable of increasing the number of copies of a plasmid is present at one site, and which comprises the nucleotide sequence of SEQ ID NO: 2.

(11) The DNA fragment of (9), wherein a mutation point capable of increasing the number of copies of a plasmid is present at one site, and which comprises the nucleotide sequence of SEQ ID NO: 4.

(12) The DNA fragment of (9), wherein a mutation point capable of increasing the number of copies of a plasmid is present at one site, and which comprises the nucleotide sequence of SEQ ID NO: 9.

(13) A plasmid, which carries the DNA fragment of any one of (9) to (12), is capable of autonomously replicating within the bacteria of the genus *Rhodococcus*, and can be present in a number of copies.

(14) A plasmid pLK006, which carries the DNA fragment of claim 11, is capable of autonomously replicating within the bacteria of the genus *Rhodococcus*, and can be present in a number of copies.

The DNA fragment of the present invention (hereinafter referred to as a multiple-copy plasmid DNA fragment), which contains a gene having a function relating to the autonomous replication of a plasmid within the bacteria of the genus *Rhodococcus* and wherein a mutation point capable of increasing the number of copies of a plasmid is present in at least one site in the gene means a DNA fragment which contains a gene having a function relating to the autonomous replication of a plasmid and has an action that can increase the number of copies of a plasmid vector that is produced using a DNA fragment having a mutation point, compared with the number of copies of a plasmid vector that is produced using a DNA fragment having no mutation point. In this specification, the term "number of copies" means the number of plasmid molecules per cell (the number of existing plasmids). The term "a number of copies" means the number of copies which is greater than the number of copies of a plasmid vector that is produced using a DNA fragment containing a gene having a function relating to the autonomous replication of a plasmid and having no mutation point.

The multiple-copy plasmid DNA fragment of the present invention can be obtained from a plasmid that autonomously replicates within the bacteria of the genus *Rhodococcus* or a DNA fragment containing a gene having a function relating to the autonomous replication of a plasmid, both of which are appropriately treated to cause mutations.

Normally, a plasmid that autonomously replicates within the bacteria of the genus *Rhodococcus* or a DNA fragment containing a gene having a function relating to the autonomous replication of a plasmid is inserted by a known method into a vector plasmid having a drug resistance gene that can be a marker. Examples include pHSG298 (TAKARA SHUZO) having a kanamycin resistance gene, pHSG398 (TAKARA SHUZO) having a chloramphenicol resistance gene, pBR322 (TAKARA SHUZO) having a tetracycline resistance gene, and pUC18 (TAKARA SHUZO) having an ampicillin resistance gene. The vector plasmid was then transformed into a host bacterium of the genus *Rhodococcus* by electroporation method. Plasmid DNA is extracted from the resulting transformant by a known method such as an alkaline SDS method, and then a target DNA fragment can be confirmed by, for example, analyzing fragments treated with restriction enzymes.

Appropriate treatment to cause mutations means to irradiate bacteria carrying the plasmids prepared as described above with ultraviolet rays, X-rays, γ-rays or the like, or to treat the same with a mutation-causing agent such as N-methyl-N'-nitrosoguanidine. Furthermore, spontaneous mutations that occur when an organism proliferates can also be utilized.

Alternatively, a plasmid that autonomously replicates within the bacteria of the genus *Rhodococcus* or a DNA fragment containing a gene having a function relating to the autonomous replication of a plasmid is directly, or after treatment to make it a single-stranded DNA with hydrazine, formic acid or nitrous acid. Alternatively, it is also effective to select an appropriate primer, and then directly introduce a mutation into a DNA fragment by a known method including error-prone PCR or the like wherein PCR is performed in the presence of a nucleotide analog or a manganese ion. According to this method, a mutation can be intensively introduced at a certain position of a DNA sequence. Thus, for example, a mutation can be specifically introduced into the DNA fragment, as disclosed in the present invention, containing a gene having a function relating to the autonomous replication of a plasmid. Furthermore, a DNA fragment containing a gene having a function relating to the autonomous replication of a plasmid can also be synthesized.

A recombinant carrying a plasmid vector having a drug marker gene wherein a mutation has been introduced as described above is cultured under the selection using a drug marker at various concentrations. Thus, strains that are resistant to the drug at higher concentrations are selected, so that strains with the thus increased number of copies of the plasmid can be obtained. It can be considered that the elevated drug concentrations, to which such strains are resistant, result from a gene amplification effect brought by an increased number of copies of the plasmid. Multiple-copy plasmid DNA fragments can be obtained by collecting plasmids from such strains.

In the case of a plasmid that autonomously replicates within the bacteria of the genus *Rhodococcus* or a DNA fragment containing a gene having a function relating to the autonomous replication of a plasmid, which have been treated to cause mutations, the above-mentioned plasmid vector having an appropriate drug resistance gene is inserted, and then transformation of a host bacterium of the genus *Rhodococcus* is performed by electroporation method. The host bacteria are cultured under the selection using a drug marker at various concentrations so as to select strains that are resistant to the drug at higher concentrations. Thus, strains with an increased number of copies of the plasmid can be obtained.

It is convenient to use a drug resistance gene as a marker gene. A known method using alkaline phosphatase, luciferase, lacZ genes or the like that enables simple detection can also be used.

The number of copies can be analyzed according to, for example, a method described in Journal of Bacteriology, 152, p. 722 (1982). Specifically, analysis can be performed by extracting chromosomal DNA and plasmid DNA from cells, and then finding the ratio of the number of molecules of both DNAs. More simply, the number of copies can be compared by culturing a recombinant carrying a plasmid having no mutation point and a recombinant carrying a plasmid having a mutation point under the same conditions, extracting plasmids, performing agarose electrophoresis, staining with ethidium bromide or the like, and then analyzing densitometry.

SEQ ID NO: 1 shows the result of determining the nucleotide sequence of plasmid pRC004 derived from *Rhodococcus rhodochrous* IFO 3338. Based on the nucleotide sequence information, 2 open reading frames (ORF) are deduced to be present in PRC004. One ORF (the putative amino acid sequence is shown in SEQ ID NO: 6) is deduced to be encoded by 921 nucleotides (the 1142nd to the 2062nd nucleotides in the nucleotide sequence of SEQ ID NO: 1) represented by SEQ ID NO: 5. This ORF is analogous to Rep A protein involved in the replication of pKA22 plasmid derived from *Rhodococcus rhodochrous* NCIMB13064 and pAL5000 plasmid derived from *Mycobacterium fortuitum*. The other ORF (the putative amino acid sequence is shown in SEQ ID NO: 8) is deduced to be encoded by 282 nucleotides (the 2052nd to the 2333rd nucleotides in SEQ ID NO: 1) represented by SEQ ID NO: 7. This ORF is analogous to the ORF deduced to be a DNA-binding plasmid replication factor of plasmid pFAJ2600 derived from *Rhodococcus erythropolis* N186/21. However, the above discussion is based on genetic similarity, and their functions have not been determined. Thus they are likely to be pseudogenes that do not actually function.

According to the present invention, it was revealed for the first time that an approximately 1.6-kb DNA fragment (SEQ ID NO: 3) produced by cleavage of pRC004 with Spl I and Sac I is a region containing a gene having a function relating to the autonomous replication of a plasmid within the bacteria of the genus *Rhodococcus*.

Specifically, it was revealed that an approximately 1.9-kb DNA fragment and an approximately 2.3-kb DNA fragment that are produced by cleavage of pRC004 with Sma I and Sac I, respectively, both contain a region containing a gene having a function relating to the autonomous replication of a plasmid within the bacteria of the genus *Rhodococcus*. Furthermore, when the approximately 1.9-kb DNA fragment that had been produced by cleavage with Sma I was cleaved with Sac I, and then the produced DNA fragment of approximately 1.7 kb was examined, it was revealed that this DNA fragment also contains a region containing a gene having a function relating to the autonomous replication of a plasmid within the bacteria of the genus *Rhodococcus*. It was also revealed that an approximately 1.6-kb DNA fragment produced by cleavage of the approximately 1.7-kb DNA fragment with Spl I contains a region containing a gene having a function relating to the autonomous replication of a plasmid within the bacteria of the genus *Rhodococcus*.

When Bam HI, Bgl II, Sph I and Xho I recognition sites existing in the above DNA fragment of approximately 1.6 kb having cleavage points for restriction enzymes Spl I and Sac I at its ends were respectively cleaved with each of their corresponding restriction enzymes, treated with klenow fragments and the like for blunt-ending to perform self-ligation, the autonomous replication function of the plasmid within the bacteria of the genus *Rhodococcus* was lost. Thus, it was revealed that a protein factor capable of actually functioning is present in this region.

Furthermore, the finding that introduction of a mutation point to at least one site in the DNA fragment of pRC004 can increase the number of copies of a plasmid has been disclosed for the first time by the present invention.

Specifically, a multi-copy variant plasmid can be obtained for the first time according to the present invention by obtaining a variant having an improved degree of resistance against kanamycin using a composite plasmid vector prepared by inserting a plasmid vector containing a kanamycin resistance gene capable of functioning as a marker into pRC004.

The discovery for the first time that a multi-copy variant plasmid can be obtained by introducing a mutation point to at least one site in a region containing a gene that has a function relating to the autonomous replication of a plasmid within the bacteria of the genus *Rhodococcus* is highly significant. We believe that this means that multi-copy variant plasmids can be easily obtained based on the present invention, and using a known method.

An example of such a multi-copy variant plasmid is plasmid pLK006 obtained in the present invention. pLK006 is a variant (SEQ ID NO: 4) wherein the 1336th guanine nucleotide is substituted with a thymine nucleotide within the region represented by SEQ ID NO: 3 among regions containing a gene having a function relating to the autonomous replication of a plasmid within the bacteria of the genus *Rhodococcus*. This corresponds to the 2262nd nucleotide of the nucleotide sequence of SEQ ID NO: 1 and the 211st nucleotide of the nucleotide sequence of SEQ ID NO: 7. SEQ ID NO: 2 and SEQ ID NO: 9 respectively represent SEQ ID NO: 1 and SEQ ID NO: 7, both of which have a mutation at one nucleotide. The putative amino acid sequence encoded by ORF is derived from SEQ ID NO: 8 by mutation (substitution) of the 71st glycine to (with) serine (SEQ ID NO: 10).

In addition, plasmid pLK006 was deposited with the International Patent Organism Depositary at the National Institute of Advanced Industrial Science and Technology (Central 6, 1-1-1, Higashi, Tsukuba, Ibaraki, Japan) on Jun. 22, 2001, under the accession number of FERM BP-8085.

Furthermore, the DNA fragment of the present invention also includes a DNA fragment that hybridizes under stringent conditions to the DNA and contains a gene having a function relating to the autonomous replication of a plasmid within the bacteria of the genus *Rhodococcus*, or a DNA fragment that hybridizes under stringent conditions to the DNA and contains a gene that has a function relating to the autonomous replication of a plasmid within the bacteria of the genus *Rhodococcus* and wherein a mutation point capable increasing the number of copies of a plasmid is present in at least one site. Here, stringent conditions mean conditions wherein so-called a specific hybrid is formed, but no non-specific hybrid is formed. Under such conditions, DNAs sharing high homology, such as DNAs having homology of at least 60% or more, preferably 80% or more, and further preferably 95% or more, hybridize to each other. However, DNAs having homology lower than the above homologies do not hybridize to each other. Alternatively, another example of the stringent conditions wherein DNAs hybridize to each other is the washing condition for normal Southern hybridization consisting of 60° C., 1×SSC and 0.1% SSD, or preferably consisting of a salt concentration corresponding to 0.1×SSC and 0.1% SDS. Such DNA can be obtained by altering the nucleotide sequence of the DNA fragment of the present invention by, for example, a site-directed mutagenesis method.

BEST MODE FOR CARRYING OUT THE INVENTION

Figure 1:
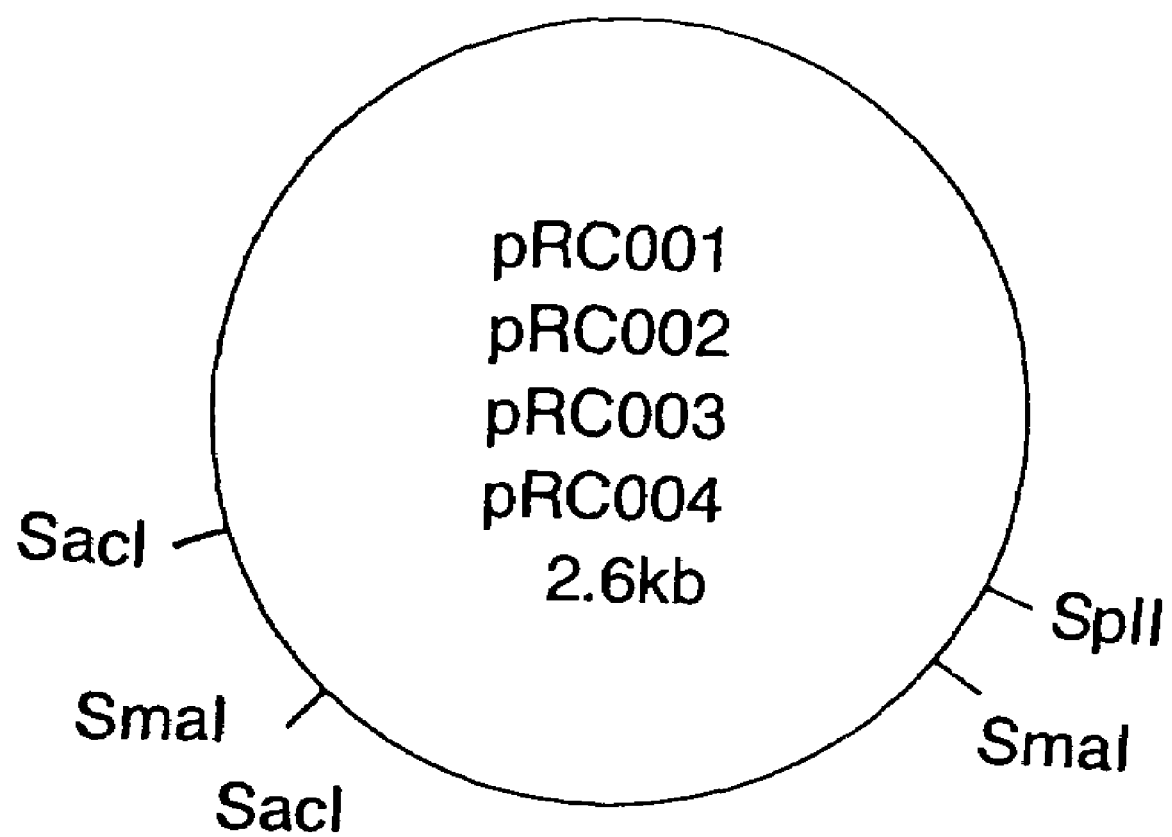
FIG. 1 shows the restriction enzyme fragment map of plasmids pRC001, pRC002, pRC003 and pRC004.

The present invention will be described more specifically by the following examples. These examples are not intended to limit the technical scope of the present invention.

EXAMPLE 1

Preparation of a DNA fragment of pRC004 containing a gene having a function relating to the autonomous replication of a plasmid within the bacteria of the genus *Rhodococcus*.

Plasmid pRC004 (1 µg) extracted from *Rhodococcus rhodochrous* IFO 3338 was allowed to react at 37° C. for 1 hour with 5 units of restriction enzyme Sma I or Sac I that had been added thereto, so as to cleave the plasmid DNA. The solution of the plasmid cleaved with the restriction enzyme was subjected to 0.7% agarose gel electrophoresis. From the product cleaved with Sma I, approximately 650 bp or approximately 1.9-kb DNA fraction was excised. From the product cleaved with Sac I, approximately 300 bp or approximately 2.3-kb DNA fragment was excised.

In the meantime, 0.5 µg of plasmid vector pHSG299 (TAKARA SHUZO) having a kanamycin resistance gene was allowed to react at 37° C. for 1 hour with 5 units of restriction enzyme Sma I or Sac I that had been added thereto, so as to cleave the plasmid DNA. A one-tenth volume of 1 M-Tris-HCl (pH9.0) was added to the reaction solution, and then allowed to react with alkaline phosphatase (1 unit) at 65° C. for 1 hour. The solution of the plasmid vector cleaved with the restriction enzyme was subjected to 0.7% agarose gel electrophoresis, and 2.7-kb DNA fragments were excised.

Upon the excision of the DNA fragments, lambda phage DNA digested with Hind III was used as a size marker, so that the size of DNA was calculated. DNA was extracted from the agarose gel using a Gene clean kit (FUNAKOSHI), and then dissolved in TE buffer (10 mM Tris-HCl, 1 mM EDTA, (pH8.0)).

The solutions containing each DNA fragment were mixed in an equivalent volume. Then each component was added to the solution to achieve T4 DNA ligase (1 unit), 1 mM ATP, 10 mM dithiothreitol and 10 mM $MgCl_2$, followed by reaction at 4° C. overnight.

The above reaction solution was added to the competent cells (TAKARA SHUZO) of the *Escherichia coli* JM105 strain. The resultant was allowed to stand at 0° C. for 1 hour, and then subjected to heat treatment at 42° C. for 2 minutes. 2×YT medium (0.5% NaCl, 1% yeast extract and 1.6% trypton) was added to the solution, and then shaken at 37° C. for 1 hour. The solution was spread on 2×YT agar medium containing 25 µg/ml kanamycin, 1 mM IPTG (isopropyl-β-galactopyranoside) and 0.02% X-gal (5-bromo-4-chloro-3-indolyl-β-D-galactopyranoside) was coated with the solution, and then the agar medium was allowed to stand at 37° C. overnight. White colonies were selected from the colonies that had appeared, and then shake-cultured in 2×YT medium (3 ml) containing 50 µg/ml kanamycin at 37° C. for 8 hours.

Cells were collected by centrifugation at 15,000 rpm for 5 minutes, and then suspended in 0.35 ml of STET solution (8% sucrose, 0.5% TritonX-100, 50 mM EDTA and 10 mM Tris-HCl (pH8.0)). 25 µl of lysozyme solution (10 mg/ml) was added to the suspension. After agitation with Vortex for 3 seconds, the product was immersed in boiling hot water for 50 seconds. Centrifugation was performed at 15,000 rpm for 15 minutes to remove the precipitate, so that the supernatant was obtained. 0.5 ml of TE saturated phenol:chloroform (1:1) solution was added to the supernatant. After agitation, centrifugation was performed at 15,000 rpm for 5 minutes, so that the upper layer was obtained. 0.5 ml of diethyl ether was added and mixed, and then centrifugation was performed to remove the upper layer. 0.5 ml of isopropanol and 50 µl of 2.5 M sodium acetate solution (pH 4.5) were added, and then the solution was allowed to stand at −80° C. for 30 minutes. Then, centrifugation was performed at 15,000 rpm for 10 minutes, so that the precipitate was obtained. The precipitate was washed with 70% ethanol, dried under reduced pressure, and then dissolved in 0.1 ml of TE buffer.

Using the above plasmid solution prepared as described above, cleavage was performed with restriction enzyme Sma I or Sac I, thereby confirming that the target DNA fragments had been inserted. Using plasmids each having a different DNA fragment inserted therein, and *Rhodococcus rhodochrous* ATCC12674 as a host, transformation was performed by electroporation method.

Transformation according to electroporation method was performed by the following methods. Cells at the logarithmic growth phase of the *Rhodococcus rhodochrous* ATCC12674 strain were collected with a centrifugal separator, washed 3 times with ice-cooled sterilized water, and then suspended in sterilized water. 1 µl of the above plasmid and 10 µl of the cell suspension were mixed, and then ice-cooled. The suspension of DNA and the cell was put into a cuvette, and then subjected to electric pulse treatment (at 2.0 kV and 200 OHMS) using a gene transfer system (Gene Pulser (BIO RAD)). The solution treated with electric pulses was allowed to stand for 10 minutes while cooling with ice. Then heat shock was performed at 37° C. for 10 minutes, and then 500 µl of MYK medium (0.5% polypeptone, 0.3% bactoyeast extract, 0.3% bacto malt extract, 0.2% $K_2HPO_4$ and 0.2% $KH_2PO_4$) was added. After the solution had been allowed to stand at 30° C. for 5 hours, the solution was spread on MYK agar medium containing 50 mg/L kanamycin and then the agar medium was allowed to stand at 30° C. for 3 days.

Table 1 shows plasmids used herein and whether or not transformants could be obtained. When a plasmid prepared by inserting an approximately 1.9-kb Sma I-cleaved fragment and an approximately 2.3-kb Sac I-cleaved fragment of pRC004 into a plasmid vector pHSG299 was used, a kanamycin-resistant recombinant was obtained. Plasmids were extracted from the obtained recombinants, and then analyzed by agarose electrophoresis. Thus, plasmids each having the same molecular weights as those of the plasmids used for transformation were obtained.

TABLE 1

| Plasmid used | | Whether or not kanamycin-resistant transformant was obtained |
|---|---|---|
| Sma I | 650 bp + pHSG299 | not obtained |
| Sma I | 1.9 kb + pHSG299 | obtained |
| Sac I | 300 bp + pHSG299 | not obtained |
| Sac I | 2.3 kb + pHSG299 | obtained |

EXAMPLE 2

In a manner similar to that of Example 1, plasmid pRC004 (1 µg) extracted from *Rhodococcus rhodochrous* IFO 3338 was allowed to react at 37° C. for 1 hour with 5 units of restriction enzymes Sma I and Sac I that had been added thereto, so as to cleave the plasmid DNA. The solution of the plasmid cleaved with the restriction enzymes was subjected to 0.7% agarose gel electrophoresis, so that an approximately 1.7-kb DNA fragment was excised.

In the meantime, 0.5 µg of plasmid vector pHSG299 (TAKARA SHUZO) having a kanamycin resistance gene was allowed to react at 37° C. for 1 hour with 5 units of restriction enzymes Sma I and Sac I that had been added thereto, so as to cleave the plasmid DNA. A one-tenth volume of 1M-Tris-HCl (pH 9.0) was added to the reaction solution, and then the resultant was allowed to react with alkaline phosphatase (1 unit) at 65° C. for 1 hour. The solution of the plasmid vector cleaved with the restriction enzymes was subjected to 0.7% agarose gel electrophoresis, so that a 2.7-kb DNA fragment was excised.

The solutions each containing different DNA fragments were mixed in an equivalent volume, and then each component was added to the solution to achieve T4 DNA ligase (1 unit), 1 mM ATP, 10 mM dithiothreitol and 10 mM $MgCl_2$. The solution was allowed to react at 4° C. overnight.

*Escherichia coli* JM105 was transformed with the above reaction solution, so that a plasmid having the above DNA fragment of approximately 1.7 kb inserted therein was obtained. *Rhodococcus rhodochrous* ATCC12674 was transformed by electroporation method using the obtained plasmid, so that a kanamycin-resistant transformant could be obtained.

EXAMPLE 3

The plasmid obtained in Example 2 was allowed to react at 37° C. for 1 hour with 5 units of restriction enzymes Spl I and Sma I that had been added thereto, so as to cleave the plasmid DNA. The cleaved plasmid was collected by ethanol precipitation and blunt-ended by the addition of 5 units of klenow fragments. Each component was added to the product to achieve T4 DNA ligase (1 unit), 1 mM ATP, 10 mM dithiothreitol and 10 mM $MgCl_2$, followed by reaction at 4° C. overnight.

*Escherichia coli* JM105 was transformed with the above reaction solution, so that a plasmid having the above DNA fragment of approximately 1.6 kb inserted therein was obtained. *Rhodococcus rhodochrous* ATCC12674 was transformed by electroporation method using the obtained plasmid, so that a kanamycin-resistant transformant could be obtained.

EXAMPLE 4

Obtainment of Multi-Copy Plasmid DNA Fragment

*Rhodococcus* sp N775 (deposited with the International Patent Organism Depositary at the National Institute of Advanced Industrial Science and Technology (Central 6, 1-1-1, Higashi, Tsukuba, Ibaraki, Japan) on Jan. 10, 1986, under the accession number of FERM BP-961) was transformed by the electric pulse method using a composite plasmid vector pK4 consisting of plasmid pRC004 and plasmid pHSG299. The obtained transformant was cultured in 10 ml of MYK medium at 30° C. for 1 day, and then irradiated with ultraviolet rays within a clean bench so as to perform treatment to cause mutations. The treated culture solution was spread on MYK agar medium containing 50 to 400 μg/ml kanamycin, and then the agar medium was allowed to stand at 30° C. for 3 days.

Colonies that had grown were cultured, so that plasmids were extracted. *Rhodococcus* sp N775 was transformed again using the extracted plasmid, and then it was checked whether or not the transformant was resistant to kanamycin at a higher concentration. Several strains of the recombinants having clearly improved resistance to kanamycin, that is, those resistant to higher kanamycin concentrations, were obtained. Chromosomes and plasmid DNAs were prepared from the pLK006 strain, one of the obtained recombinants, and the recombinant transformed with composite vector pK4 having no mutation points. When the number of copies of the plasmids was then compared, the number of copies in pLK006 obtained by treatment to cause mutations was found to be elevated to a level approximately 5 times greater than that of pK4.

Of the above microorganisms, gene recombinants that we had prepared were deposited under the above number with the International Patent Organism Depositary at the National Institute of Advanced Industrial Science and Technology.

EXAMPLE 5

Determination of Mutation Point

The nucleotide sequence of the multi-copy variant plasmid pLK006 obtained in Example 3 was determined using a fluorescence sequencer ALFII (Pharmacia). As a result, the nucleotide sequence represented by SEQ ID NO: 4 was obtained.

In the region represented by SEQ ID NO: 2, the 1336th guanine nucleotide was mutated to (substituted with) a thymine nucleotide.

INDUSTRIAL APPLICABILITY

Introduction of a useful gene into the multi-copy-number plasmid vector, which is provided by the present invention, using the bacterium of the genus *Rhodococcus* as a host makes it possible to improve the expression level of the useful gene. The thus obtained gene recombinant having the improved expression level of a useful gene is industrially very useful.

All publications, patents and patent applications cited herein are incorporated herein by reference in their entirety. It is therefore readily to be understood by a person skilled in the art that numerous modifications and variations of the present invention are possible within the scope of the invention without departing from the technical idea and the scope of the invention as described in the appended claims. The present invention is intended to encompass such modifications and variations.

---

The invention claimed is:

1. An isolated polynucleotide which is at least 95% homologous to SEQ ID NO: 7 or which hybridizes to the full complement of SEQ ID NO: 7 under stringent conditions, wherein stringent conditions comprise washing in 0.1×SSC and 0.1% SDS at 60° C.;
   wherein said isolated polynucleotide contains a point mutation of the polynucleotide sequence of SEQ ID NO: 7 and the point mutation changes the 71$^{st}$ Gly of the amino acid sequence of SEQ ID NO: 8 to Ser, and
   wherein the isolated polynucleotide increases plasmid copy number when incorporated into plasmid in *Rhodococcus* when compared to the plasmid copy number in *Rhodococcus* containing a plasmid having the unaltered polynucleotide sequence of SEQ ID NO: 7.

2. The isolated polynucleotide of claim 1, which comprises a point mutation at nucleotide 211 of SEQ ID NO: 7 so that nucleotide 211 is thymine.

3. A vector comprising the isolated polynucleotide of claim 1 or 2.

4. An isolated host cell comprising the vector of claim 3.

5. The isolated host cell of claim 4 which is *Rhodococcus*.

6. A method for increasing plasmid copy number in *Rhodococcus* comprising transforming a *Rhodococcus* cell with the vector of claim 3.

7. An isolated polynucleotide which comprises SEQ ID NO: 2.

8. An isolated polynucleotide which comprises SEQ ID NO: 9.

9. A vector comprising the isolated polynucleotide of claim 7 or 8.

10. An isolated host cell comprising the vector of claim 9.

11. The isolated host cell of claim 10 which is *Rhodococcus*.

12. A method for increasing plasmid copy number in *Rhodococcus* comprising transforming a *Rhodococcus* cell with the vector of claim 9.

13. Plasmid pLK006 identified by accession number FERM BP-8085.

* * * * *